US012716898B2

(12) United States Patent
Fagiola et al.

(10) Patent No.: US 12,716,898 B2
(45) Date of Patent: Aug. 25, 2026

(54) METHOD FOR MEASURING COPD BIOMARKERS

(71) Applicant: ST. JOHN'S UNIVERSITY, Queens, NY (US)

(72) Inventors: Michael Fagiola, Queens, NY (US); Jerome Cantor, Queens, NY (US)

(73) Assignee: ST. JOHN'S UNIVERSITY, Queens, NY (US)

(*) Notice: Subject to any disclaimer, the term of this patent is extended or adjusted under 35 U.S.C. 154(b) by 1038 days.

(21) Appl. No.: 17/821,672

(22) Filed: Aug. 23, 2022

(65) Prior Publication Data

US 2023/0030026 A1 Feb. 2, 2023

Related U.S. Application Data

(63) Continuation of application No. PCT/US2022/034974, filed on Jun. 24, 2022.

(Continued)

(51) Int. Cl.
*G01N 33/00* (2006.01)
*G01N 1/40* (2006.01)
(Continued)

(52) U.S. Cl.
CPC ....... *G01N 33/6887* (2013.01); *G01N 1/4077* (2013.01); *G01N 30/7233* (2013.01);
(Continued)

(58) Field of Classification Search
CPC .................................................. G01N 33/6887
(Continued)

(56) References Cited

U.S. PATENT DOCUMENTS 7,947,037 B1 * 5/2011 Garito .................... A61B 18/14 606/49
8,444,624 B2 * 5/2013 Ogle ..................... A61M 25/10 604/509
2006/0014698 A1 * 1/2006 O'Connor ............ A61K 9/0078 514/1.7

FOREIGN PATENT DOCUMENTS

EP 1839648 A2 * 10/2007 .............. A61P 37/06
JP 2014119370 A * 6/2014
(Continued)

OTHER PUBLICATIONS

English Translation of JP 2014119370 A obtained from google on Aug. 26, 2025 (Year: 2025).*
(Continued)

*Primary Examiner* — Lyle Alexander
*Assistant Examiner* — Emily R. Berkeley
(74) *Attorney, Agent, or Firm* — VENABLE LLP

(57) ABSTRACT

The invention pertains to the use of a specific biomarker of elastin degradation (desmosine) that measures the extent and progression of chronic obstructive pulmonary disease (COPD). In addition to potentially serving as a screening procedure for COPD, it provides a real-time measure of COPD drug efficacy and may therefore supersede the use of less sensitive tests such as pulmonary function studies and computed tomography. Equally important, the current invention constitutes a marked improvement for measuring desmosine in tissues and body fluids by greatly shortening the time for detection of this molecule in liquid chromatography-tandem mass spectrometry (LC-MS-MS) assays that are the gold standard for such measurements. Unlike previous methods, the invention allows for the use of LC-MS-MS without modification, so the method can be applied to any laboratory that uses this equipment for other measurements.

(Continued)

This would include forensic facilities that need to determine if undiagnosed COPD played a role in the loss of life.

18 Claims, 5 Drawing Sheets

Related U.S. Application Data

(60) Provisional application No. 63/226,502, filed on Jul. 28, 2021.

(51) Int. Cl.
*G01N 30/72* (2006.01)
*G01N 30/88* (2006.01)
*G01N 33/68* (2006.01)
*A61B 5/00* (2006.01)
*G01N 30/02* (2006.01)

(52) U.S. Cl.
CPC ............ *G01N 30/88* (2013.01); *A61B 5/4848* (2013.01); *G01N 2001/4083* (2013.01); *G01N 2030/027* (2013.01); *G01N 2030/8818* (2013.01); *G01N 2333/78* (2013.01); *G01N 2800/10* (2013.01); *G01N 2800/122* (2013.01)

(58) Field of Classification Search
USPC .......................................................... 436/89
See application file for complete search history.

(56) References Cited

FOREIGN PATENT DOCUMENTS

WO 2011/094343 A1 8/2011
WO 2014/179408 A1 11/2014

OTHER PUBLICATIONS

Akagawa, M., et al., (2000) Mechanism of Formation of Elastin Crosslinks. Connective Tissue Research, 41, 131-141.
Albarbarawi, O., et al., (2013) Characterization and validation of an isotope-dilution LC-MS/MS method for quantification of total desmosine and isodesmosine in plasma and serum. Bioanalysis, 5, 1991-2001.
ASB AAFS Standards Board (2019) ANSI/ASB Standard 036: Standard Practices for Method Validation in Forensic Toxicology (accessed Jan. 14, 2021).
Cantor, J., et al. (2017) A pilot clinical trial to determine the safety and efficacy of aerosolized hyaluronan as a treatment for COPD. International Journal of Chronic Obstructive Pulmonary Disease, 12, 2747-2752.
Cantor, J., et al. (2018) Free Desmosine is a Sensitive Marker of Smoke-Induced Emphysema. Lung, 196, 659-663.
Cantor, J., et al. (2021) A 28-day clinical trial of aerosolized hyaluronan in alpha-1 antiprotease deficiency COPD using desmosine as a surrogate marker for drug efficacy. Respiratory Medicine, 182, 1-7.
Cocci, F., et al. (2002) Urinary desmosine excretion is inversely correlated with the extent of emphysema in patients with chronic obstructive pulmonary disease. The International Journal of Biochemistry & Cell Biology, 34, 594-604.
Cumiskey, W.R., et al. (1995) Enrichment and analysis of desmosine and isodesmosine in biological fluids. Journal of Chromatography B, 668, 199-207.
Knudsen, et al. (2010) Assessment of air space size characteristics by intercept (chord) measurement: an accurate and efficient sterological approach. Journal of Applied Physiology, 108, 412-421.
Luisetti, M., et al. (1996) MR889, a neutrophil elastase inhibitor, in patients with chronic obstructive pulmonary disease: a double-blind, randomized, placebo-controlled clinical trial. European Respiratory Journal, 9, 1482-1486.
Luisetti, M., et al. (2012) Desmosine, a biomarker for COPD: old and in the way. European Respiratory Journal, 39, 797-798.
Ma, S., et al. (2011) Quantitation of desmosine and isodesmosine in urine, plasma, and sputum by LC-MS/MS as biomarkers for elastin degradation. Journal of Chromatography B, 879, 1893-1898.
Ma, S., et al. (2013) Stable deuterium internal standard for the isotope-dilution LC-MS/MS analysis of elastin degradation. Analytical Biochemistry, 440, 158-165.
Mcclintock, D.E., et al. (1995) Higher urine desmosine levels are associated with mortality in patients with acute lung injury. American Journal of Physiology—Lung Cellular and Molecular Physiology, 291, 566-571.
Mecham, R.P., (1997) Elastin fibers in the lung. In R.G. Crystal, J.B. West, E.R. Weibel, P.J. Barnes (eds.), Scientific Foundations, Lippincott-Raven, Philadelphia, PA, pp. 729-736.
Mehraban, S., et al. (2020) The Proinflammatory Activity of Structurally Altered Elastic Fibers. American Journal of Respiratory Cell and Molecular Biology, 63, 699-706.
Shimada, W., et al. (1969) An approach to the study of the structure of desmosine and isodesmosine containing peptides isolated from the elastase digest of elastin. Biochemical and Biophysical Research Communications, 37, 191-197.
Starcher, B., et al. (1995) Measurement of urinary desmosine as an indicator of acute pulmonary disease. Respiration, 62, 252-257.
Stone, P.J., et al. (1991) Measurement of urinary desmosine by isotope dilution and high performance liquid chromatography: correlation between elastase-induced air-space enlargement in the hamster and elevation of urinary desmosine. The American Review of Respiratory Diseases, 144, 284-290.
Stone, P.J., et al. (1995) Elastin and collagen degradation products in urine of patients with cystic fibrosis. American Journal of Respiratory and Critical Care Medicine, 152, 157-162.
Stone, P.J., et al. (1995) Elastin and collagen degradation products in urine of smokers with and without chronic obstructive pulmonary diseases. American Journal of Respiratory and Critical Care Medicine, 151, 952-959.
Thomas, J., et al. (1963) Degradation Products from Elastin: Partial Structure of Two Major Degradation Products from the Cross-Linkages in Elastin. Nature, 200, 651-652.
Albarbarawai, O., et al., Measurement of Urinary Total Desmosine and Isodesmosine Using Isotope-Dilution Liquid Chromatography-Tandem Mass Spectrometry, Analytical Chemistry, vol. 82, No. 9, May 2010, 3745-3750.
Birdsall, R., et al., Application of Mobile Phase Additives to Reduce Metal-lon Mediated Adsorption of Non-Phosphorylated Peptides in RPLC/MS-Based Assays, Journal of Chromatography B 1126-1127 (2019), 1-8.
Getie, M., et al., LC/ESI-MS Analysis of Two Elastin Cross-Links, Desmosine and Isodesmosine, and Their Radiation-Induced Degradation Products, Biochimica et Biophysica Acta 1624 (2003) 81-87.
Hsiao, J., et al., Improved LC/MS Methods for the Analysis of Metal-Sensitive Analytes Using Medronic Acid as a Mobile Phase Additive, ACS Publications, 2018, 90, 9457-9464.
Ma, S., et al., Quantitation of Desmosine and Isodesmosine in Urine, Plasma, and Sputum By LC-MS/MS as Biomarkers for Elastin Degradation, Journal of Chromatography B 879 (2011) 1893-1898.
Miliotis, T., et al., Quantitative High-Performance Liquid Chromatography-Tandem Mass Spectrometry Method for the Analysis of Free Desmosines in Plasma and Urine, Journal of Chromatography A 1308 (2013) 73-78.
Chalmers et al., Neutrophil Elastase Activity is Associated with Exacerbations and Lung Function Decline in Bronchiectasis, Am J Respir Crit Care Med, vol. 195, No. 10 (2017) 1384-93.
Kuzmanova et al., Accelerating isotope dilution LC-MS-based desmosine quantification for estimating elastin turnover, Bioanalysis, vol. 17, No. 2 (2025) 99-104.

* cited by examiner

METHOD FOR MEASURING COPD BIOMARKERS

BACKGROUND OF THE INVENTION

Elastic fibers are a significant structural constituent of several major tissues in the body including skin, blood vessels and the lung. Elastin is the major structural component of elastic fibers and provides physical recoil in response to forces that deform tissue structure, thereby contributing to normal physiologic function. Elastin is additionally highly crosslinked and a normally insoluble protein.

Desmosine (shown below) is a unique pyridinium amino acid that serves as the major crosslinking molecule binding the polymeric chains of amino acids into the 3-dimensional network of elastin.

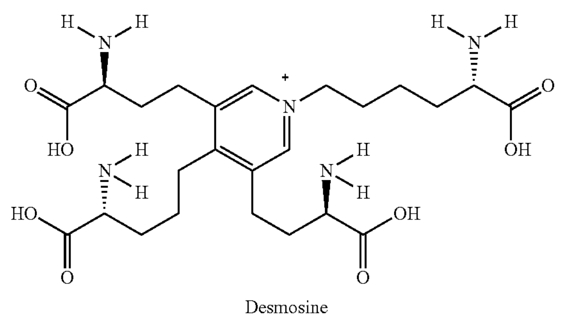

Desmosine

The degradation of tissues that contain elastin, as seen in COPD and other diseases, has been directly associated with an increased excretion of desmosine into various biological matrices, including blood, urine and sputum. Several methodologies have been developed to detect and quantify desmosine over the past two decades in these matrices. They include enzymatic and radioactive immunoassay, high performance liquid chromatography (HPLC) and liquid chromatography tandem mass spectrometry (LC-MS-MS). The increased rate of desmosine excretion as a direct result of elastin degradation has made it a potential candidate as a biomarker for COPD.

In recent years, LC-MS-MS has provided a more robust means of quantifying desmosine due in part to a greater degree of sensitivity, specificity and ease of analyzing ionized species in solution. Despite this, the precise measurement of desmosine in bodily fluids has been a challenge, as it is typically present in low concentrations. Additionally, analytical methods for the measurement of desmosine span a wide variety of techniques and may produce variable results. Quantitative inconsistency and/or poorly validated methods that may have been developed with different criteria are some of the major reasons for its lack of acceptance as a valid biomarker in COPD.

To date, there have been only limited attempts to measure desmosine directly in lung tissue by LC-MS-MS, and focusing on urine, plasma, sputum and bronchoalveolar lavage (BALF) samples. With the possible exceptions of sputum and BALF, these matrices are considered to be 'per se' indicators of elastin breakdown. Interpretation of desmosine concentrations in the aforementioned matrices is complicated in that, aside from BALF and sputum, desmosine measurements are not specific to COPD in the lung, but instead may be attributed to elastin breakdown in other diseases and from other organs where elastin turnover is also increased, e.g., heart disease and atherosclerosis.

The value of quantifying desmosine directly in lung tissue includes elucidating the biochemical changes responsible for the topological spread of emphysematous changes and the pattern of progression of COPD throughout the lung. Further, such measurements may act as a diagnostic tool for forensic pathologists in the pursuit of establishing the cause and manner of death where no apparent airway injury is present during autopsy. The extreme sensitivity of the instant mass spectrometry method suggests that measurement of free DID in lung biopsies (including transbronchial biopsies) could possibly become an accepted procedure for rapidly evaluating therapeutic agents, thereby accelerating the development of an effective treatment for COPD. While free desmosine has been measured in body fluids, the use of free tissue desmosine is entirely novel.

BRIEF SUMMARY OF THE INVENTION

Desmosine is an elastin-specific crosslink that can be isolated and quantified to determine the progression of elastic fiber damage in COPD and other disorders, including atherosclerosis, aortic aneurysm, skin lesions, cystic fibrosis, pulmonary hypertension, bronchiectasis, and chronic obstructive pulmonary disease (COPD) with and without alpha-1 antitrypsin deficiency.

This application describes a method for measuring both free and peptide-bound desmosine and isodesmosine in connective tissue matrices, plasma, urine, sputum, bronchoalveolar lavage fluid, exhaled breath condensate, formalin-fixed autopsied tissue and paraffin-embedded formalin-fixed tissue using non-ion-paired, reverse-phase LC in combination with mass spectrometry or tandem mass spectrometry to evidence its validity as a biomarker for elastin degradation and provide a method of assessing respiratory status during routine medicolegal investigations.

To further establish the usefulness of desmosine as a biomarker, we demonstrate a correlation between its concentration in the lungs of hamsters treated with cigarette smoke and LPS and the degree of pulmonary airspace enlargement.

One calibration curve using calibrators prepared in solid tissue, ranging from 40 to 2000 ng/mL (ng/g), was developed. Quality control specimens were prepared in solid tissue as well as plasma and urine to verify proper calibration of desmosine concentration. The method was evaluated for the following parameters using ANSI/ASB standards: linearity/calibration model, limits of detection, quantification, and upper limit of linearity, bias and precision, ionization suppression/enhancement, interference studies, dilution integrity, sample stability and carryover.

This method is suitable for use in forensic laboratories because validation was performed on instrumentation routinely used in this setting. Additionally, in cases where no apparent gross lung pathology may be present at autopsy, desmosine concentrations in formalin fixed tissues provide insight into the potential contribution of undiagnosed COPD to the loss of life.

DETAILED DESCRIPTION OF THE INVENTION

Figure 1:
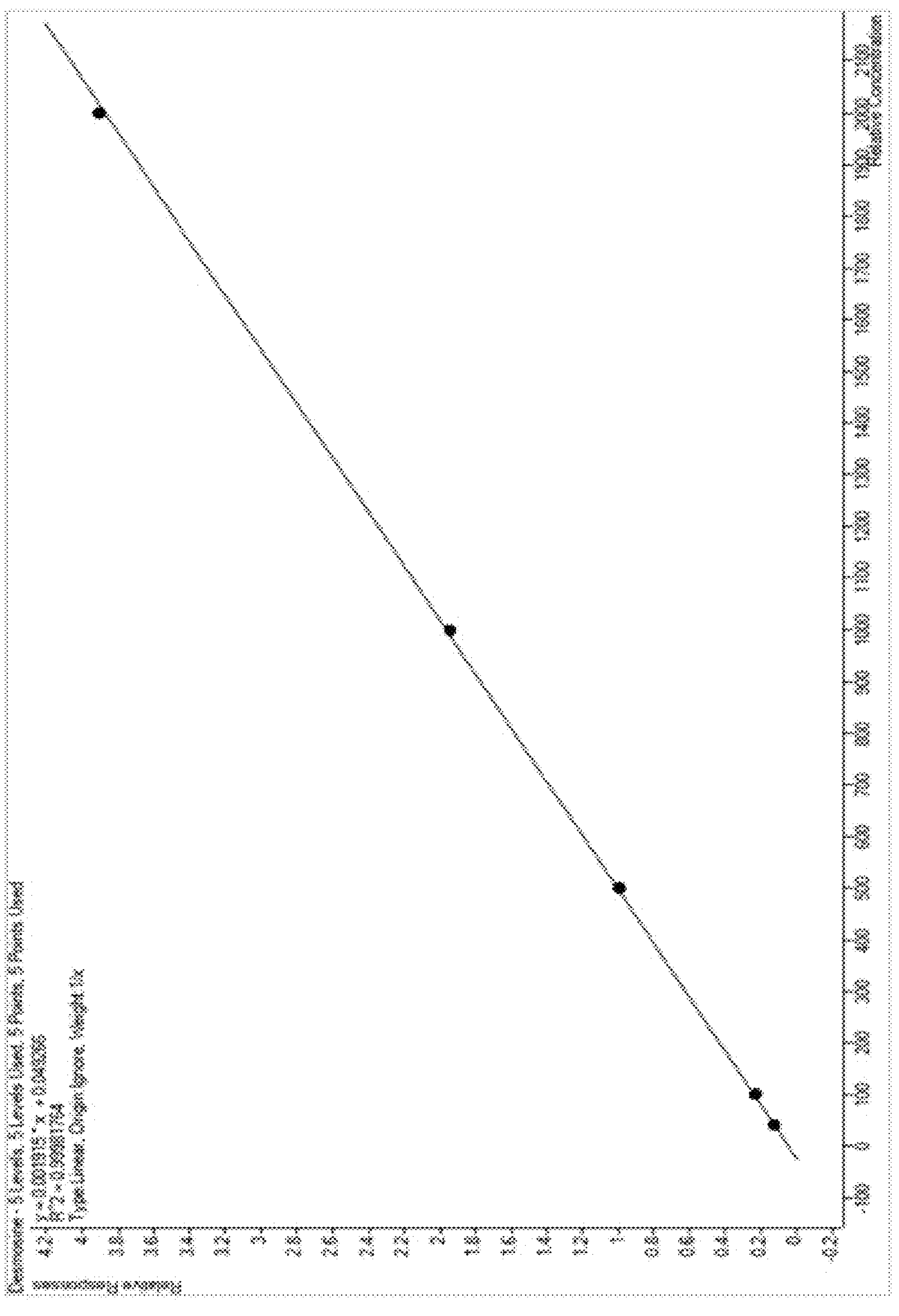
FIG. 1 is a desmosine calibration curve (40-2000 ng/ml [ng/g]).

This application describes a practical, reliable and validated method that can measure both free and peptide-bound desmosine and isodesmosine in connective tissue matrices, plasma, urine, sputum, bronchoalveolar lavage fluid, exhaled breath condensate, bronchial biopsies (including transbronchial biopsies), formalin-fixed autopsied tissue, and paraffin-embedded formalin-fixed tissue using non-ion-paired, reverse-phase LC in combination with mass spectrometry or tandem mass spectrometry involving instrumentation commonly encountered in forensic laboratories. As proof of concept, we analyzed both formalin-fixed and unfixed hamster lung specimens involving the use of lipopolysaccharide (LPS) to enhance inflammation following exposure to cigarette smoke. The results suggest that free (non-peptide-bound) desmosine released from these lungs may be a reliable means of determining the presence of pulmonary emphysema.

The method may also be used to detect and monitor elastin degradation in diseases such as atherosclerosis, aortic aneurysm, skin lesions, cystic fibrosis, pulmonary hypertension, bronchiectasis, and chronic obstructive pulmonary disease (COPD) with and without alpha-1 antitrypsin deficiency and COPD exacerbations. It therefore permits real-time assessment of the efficacy of drugs used to treat these diseases and a means of adjusting drug dosage in the above-listed diseases depending on the level of desmosine and isodesmosine in blood, urine, sputum and exhaled breath condensate.

The method may also be used to screen persons with normal lung function and smokers without a previous diagnosis of COPD for incipient pulmonary emphysema, thereby permitting early treatment intervention.

Chemicals and Reagents

A 5.0 mg commercial reference standard of desmosine was purchased from Elastin Products Company (Owensville, MO, USA) and used to prepare the calibrator working solution in water at a concentration of 1.0 mg/mL. A 1.0 mg commercial reference standard of desmosine chloride was purchased from Toronto Research Chemicals (North York, ON, CA) and used to prepare the quality control (QC) working solution in water at a concentration of 1.0 mg/mL. A 1.0 mg mass of isotopically labeled desmosine-$D_4$ was also purchased from Toronto Research Chemicals and used to prepare a reference standard at a concentration in water of 1.0 mg/mL.

Formic acid and ammonium formate were acquired from VWR Chemicals (Radnor, PA, USA) and Sigma-Aldrich (St. Louis, MO, USA). ACS and hypergrade methanol were acquired from VWR Chemicals and Millipore Sigma (Burlington, MA, USA). ACS grade hydrochloric acid and ammonium hydroxide were purchased from VWR Chemicals. Medronic acid (Infinity Lab® Deactivator Additive) was purchased from Agilent Technologies (Santa Clara, CA, USA). Ultrapure water was acquired in-house using a Milli-Q Direct 16 Water Purification System from Millipore Sigma. All solvents employed were ultra-performance liquid chromatography (UPLC) or LC-MS grade in the chromatographic system.

Standard and Control Preparation

Desmosine calibrator and QC working solutions were prepared in methanol from the purchased reference standards at concentrations of 4.0 μg/mL each. A desmosine-$D_4$ internal standard working solution was also prepared in methanol at a concentration of 10.0 μg/mL. All working solutions were stored in amber vials at <0° C. when not in use. Individual calibrator samples were prepared by fortifying solid tissue specimens prepared from sheep brain homogenate (Carolina Biological Supply Company, Burlington, NC, USA) at concentrations of 40, 100, 500, 1000 and 2000 ng/ml (ng/g). Three positive QC specimens with target concentrations of 150, 400 and 800 ng/ml (ng/g) in donor plasma (UTAK Laboratories Inc., Valencia, CA, USA), donor urine (UTAK Laboratories Inc.) and tissue, respectively, as well as a negative tissue QC sample containing only the internal standard were analyzed to verify the calibration. A high control sample containing 2500 ng/mL (ng/g) of desmosine was analyzed to assess for carryover.

Sheep brain was selected as the matrix of choice to prepare the calibration curve. Brain is comprised of predominantly fatty tissue with a quantitatively negligible amount of elastin and serves to account for potential matrix effects encountered in solid tissue specimens while also eliminating the concern of endogenous desmosine potentially contributing to the detector signal. 5 g of sheep brain was weighed and added to 50 mL plastic centrifuge tubes containing 20 mL of ultrapure water. This mixture was mechanically homogenized followed by centrifugation for 20 min at 3000 rpm. 1 mL of the resultant supernatant was then aliquoted into 15 mL plastic centrifuge tubes and fortified with the internal standard, calibrator, and QC working solutions as described above. Authentic solid tissue specimens were processed in the same manner as the calibrator and quality control samples and fortified only with the internal standard. 1 mL of plasma and urine were aliquoted directly and fortified with the internal standard.

Solid Phase Extraction Procedure

The authors have recently described a novel solid phase extraction (SPE) procedure for the extraction of desmosine and its deuterated analog in which desmosine and desmosine-$D_4$ were extracted from the aforementioned biological matrices by cationic exchange SPE utilizing Styre Screen® BCX Extraction Columns (United Chemical Technologies Inc., Bristol, PA, USA). The cation exchange sorbent serves to retain desmosine and desmosine-$D_4$. First, 3 mL of 0.1N HCl (PH ~1.0) was added to 1 mL of fortified calibrator/QC and authentic/unknown samples, followed by a quick vortex and centrifugation for 10 min at 3000 rpm prior to column loading. The SPE cartridges were conditioned with 4 mL of methanol followed by 3 mL of 0.1N HCl. Subsequently, the samples (3 mL of the pre-added 0.1N HCl and 1 mL of plasma, urine, or tissue homogenate containing desmosine and demosine-$D_4$) were loaded into each designated pre-conditioned column and were allowed to drip with gravity flow. A series of wash steps were performed on each column in the order of 3 mL of 0.1N HCl and 4 mL of methanol. The columns were then allowed to dry at full vacuum for 30 seconds. Elution of desmosine and desmosine-$D_4$ was utilized with 3 mL of a solvent prepared fresh as a mixture of 95% methanol and 5% concentrated ammonium hydroxide. Eluents were evaporated to dryness under vacuum using a rotovap, and the residues were reconstituted in 200 μL of a 95:5 mixture of water and methanol and injected into the chromatographic system.

TABLE I

| LC conditions Gradient Conditions | | | |
|---|---|---|---|
| | Time (min) | Mobile Phase A- Aqueous (%) | Mobile Phase B- Organic (%) |
| 1 | 0.00 | 95% | 5% |
| 2 | 3.00 | 95% | 5% |

An Agilent 1260 LC equipped with a Poroshell 120 EC-C18 column (3.0 mm×50 mm, 2.7 μm) was utilized for the chromatographic separation of desmosine and desmosine-$D_4$. The LC column was maintained at 50° C. in the thermostated column compartment. Mobile phases consisted of (A) 0.01% formic acid, 5 mM ammonium formate and 5 μM medronic acid in Milli-Q water, and (B) 0.01% formic acid and 5 μM medronic acid in hypergrade methanol. The mobile phase flow rate was 0.25 mL/min and the instrument injection volume was 2.5 μL. The total chromatographic run time was 3 min (Table I), with a post-time of 3 min.

TABLE II

| MS-MS conditions Multiple reaction monitoring transitions of desmosine and desmosine-$D_4$ | | | | | | | |
|---|---|---|---|---|---|---|---|
| Analyte name | Precursor ion (m/z) | RT (min) | Fragmentor (V) | Production 1 (m/z) | CE 1 (V) | Production 2 (m/z) | CE 2 (V) |
| Desmosine-$D_4$ | 530.3 | 1.359 | 171 | 485.2 | 36 | N/A | N/A |
| Desmosine | 526.3 | 1.360 | 176 | 481.2 | 36 | 84.1 | 55 |

m/z, mass-to-charge ratio;
RT, retention time;
V, voltage;
CE, collision energy;
N/A, not applicable.

An Agilent Technologies 6460-triple quadrupole mass spectrometer with a dual jetstream electrospray source was operated in positive ion mode with the following parameters: drying gas temperature 325° C., nitrogen sheath gas temperature 390° C., nitrogen drying gas flow 13 L/min, nitrogen sheath gas flow 12 L/min, nebulizer pressure 35 psi, and capillary voltage 3750 V. The multiple reaction monitoring (MRM) method monitored two transitions for desmosine and one transition for desmosine-$D_4$ (Table II). All analyte-specific parameters were optimized using individual reference standards and analyzed in product ion mode to verify analyte presence.

Experimental Findings

Method Validation

The method was validated by evaluating linearity/calibration model, limits of detection, limits of quantification, upper limit of linearity, bias and precision, ionization suppression/enhancement, interferences (selectivity and specificity), dilution integrity, sample stability, and carryover. The general validation scheme was based primarily on ANSI/ASB Standard 036. All instrumental and data analysis parameters were determined prior to the start of validation as part of method development and optimization.

Linearity/Calibration Model

A suitable calibration model was determined for desmosine that was validated for quantitative analysis. A linear model with 1/x weighting was used (FIG. 1). Calibrators were first prepared at eight concentrations from 40 to 2000 ng/ml (ng/g) to assess for linearity. Following establishment of a linear calibration model through visual analysis of residual plots indicating normal random scatter around the calibration curve, five separate calibrators within the same range of 40 to 2000 ng/ml (ng/g) were prepared and extracted (and were used in the bias and precision studies). The combined data of the five non-zero concentrations evenly spaced across the calibration range with five replicates at each level analyzed in the same extraction (five replicates per level with five curves run sequentially) were used to establish the calibration model. The coefficient of determination ($r^2$) was >0.995 for desmosine. Visual inspection of the curves and residual plots indicated normal random scatter around the calibration curve. All calibrators were within +20% of their prepared concentration.

Limits of Detection (LOD) and Quantification (LOQ)

Figure 2A:
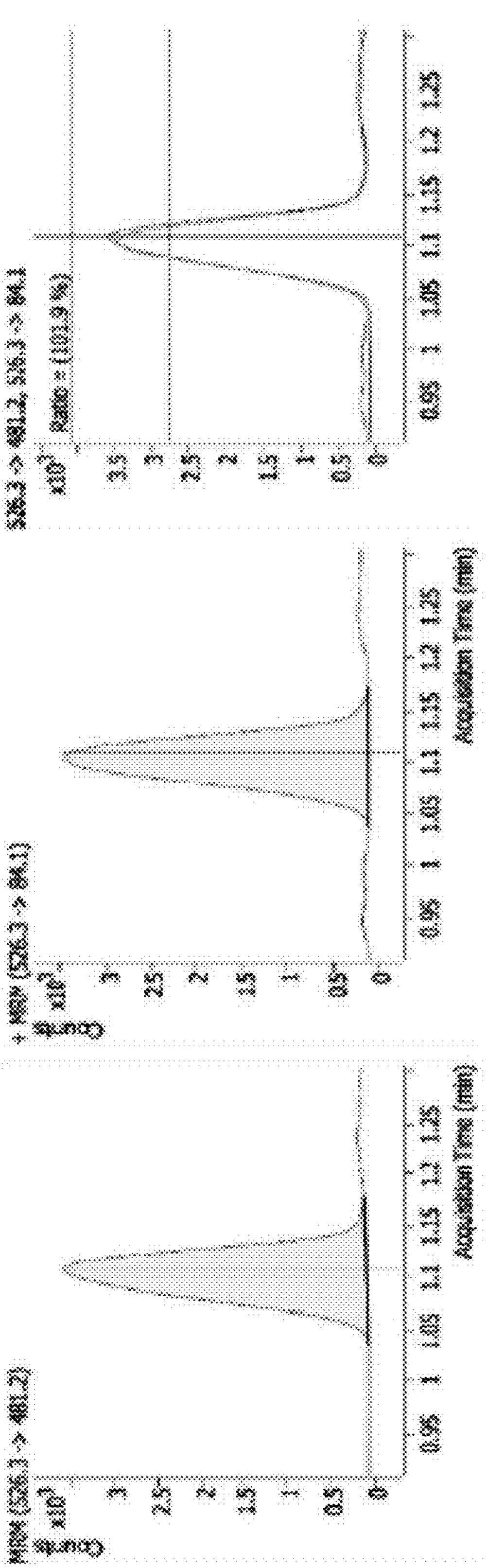
FIG. 2(A) is an extracted ion chromatogram for desmosine at its limit of detection.
Figure 2B:
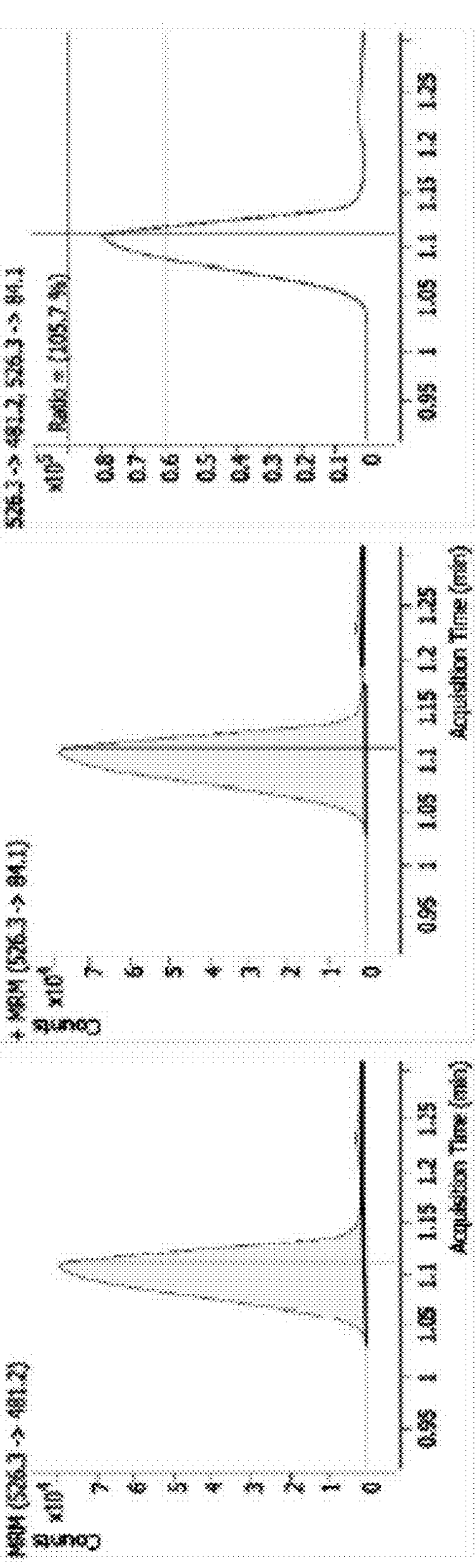
FIG. 2(B) is an extracted ion chromatogram for desmosine at its limit of quantification.

The LOD for desmosine was evaluated through the analysis of five replicates of a 20 ng/ml (ng/g) standard run in five separate extractions prepared in plasma, urine, and tissue matrices. All compounds had good chromatographic peak shape at the LODs. Signal-to-noise (S/N) for the LOD was calculated by the MassHunter® instrument software (Agilent Technologies). All S/N ratios were greater than or equal to 4:1. MRMion ratios were within +20% and retention times were within 0.1 min compared to the average of all calibrators used (FIG. 2).

The LOQ was verified by five replicates of a standard run in five separate extractions prepared in plasma, urine, and tissue matrices. All compounds had good chromatographic peak shape at the LOQ. S/N for the LOQ was also calculated by the MassHunter® instrument software. All S/N ratios were greater than or equal to 10:1. MRMion ratios were within 20% and retention times were within 0.1 min compared to the average of all calibrators. The mean bias of quantitative results was within +20% of their prepared concentration (FIG. 2).

TABLE III

Bias and precision Method Performance

| Analyte | Calibration range (ng/mL, ng/g*) | LOD (ng/mL, ng/g) | LOQ (ng/mL, ng/g) | Control Levels (ng/mL, ng/g) | Bias | | | Within-Run Precision (% CV) | | | Between-Run Precision (% CV) | | |
|---|---|---|---|---|---|---|---|---|---|---|---|---|---|
| | | | | | 150 ng/mL, ng/g n = 15 | 400 ng/mL, ng/g n = 15 | 800 ng/ml, ng/g n = 15 | 150 ng/mL, ng/g n = 6 | 400 ng/mL, ng/g n = 6 | 300 ng/mL, ng/g n = 6 | 150 ng/mL, ng/g n = 15 | 400 ng/mL, ng/g n = 15 | 800 ng/ml, ng/g n = 15 |
| Desmosine | 40-2000 | 20 | 40 | 150, 400, 800 | −4.24% | −1.63% | −1.95% | 2.02% | 1.51% | 1.04% | 4.47% | 7.03% | 3.94% |

*If measured in solid tissue, units of ng/g are used

The bias data are summarized in Table III. The bias evaluation involved the use of commercial reference material obtained from two different sources as mentioned above. The QC working solutions were fortified in plasma, urine, and tissue matrix at the low, medium, and high QC concentrations of 150, 400, and 800 ng/ml (ng/g), respectively. Three replicates in each matrix from five separate extractions were evaluated for each level. The bias was within +2% of the prepared concentrations in each matrix. The QC levels and results evaluated for desmosine is outlined in Table III.

The precision data are also summarized in Table III. Three concentration levels were evaluated (the same QC samples that were used for the bias experiments) for precision. Six replicates from five separate extractions were evaluated for each level. The method demonstrated acceptable within-run and between-run precision with all CVs <20% for desmosine.

Ionization Suppression/Enhancement

Ion suppression from potential matrix effects was assessed through a post-extraction addition method (20). Two different sets of samples were prepared, and desmosine and desmosine-$D_4$ peak areas of neat standards were compared to matrix samples fortified with neat standards after extraction. Set one consisted of neat standards prepared at two concentrations (150 or 800 ng/ml [ng/g]) in tissue, each with internal standard. Each of the neat standards was injected three times to establish a mean peak area for each concentration. Set two consisted of plasma and urine that were extracted in duplicate. After the extraction was complete, each matrix sample was fortified with the low or high concentration neat standard and internal standard. The average area of each set was used to estimate the suppression/enhancement effect at each concentration as follows for desmosine, internal standard and relative response for desmosine (quant ion/internal standard ion):

$$\text{Ionization suppression or enhancement (\%)} = \left(\frac{\overline{X}\text{ Area of Set 2}}{\overline{X}\text{ Area of Set 1}} - 1\right)x100$$

While extraction recovery for both desmosine and desmosine-$D_4$ exceeded 80%, both demonstrated ionization suppression ranging from −48% to −53%. However, the suppression was compensated for by the use of the stable isotope-labeled internal standard. The observed suppression/enhancement did not impact the LOD or LOQ as described above.

Interference Studies

As patients with COPD may be a) extensively medicated and b) have extensive lung tissue breakdown which may lead to the production of other elastin degradation products, the analytical method was evaluated for both potential endogenous and exogenous interferences using solutions containing a total of 252 non-targeted analytes. These classes of analytes include: Amino acids and elastin constituents, fentanyl and fentanyl analogs, opiates and opium-derived alkaloids, synthetic opioids, cannabinoids, benzodiazepines, antidepressants, antipsychotics, antihistamines, cocaine (and related compounds), barbiturates, muscle relaxants, anticonvulsants, Z-drugs (zaleplon, zolpidem, and zopiclone), amphetamines, cathinones, hallucinogenics, phenethylamines, dissociative anesthetics, new psychoactive substances, and other miscellaneous compounds. For a full list of analytes used in these interference studies, refer to supplementary table S1. To assess selectivity, the 252 non-target analytes were added to tissue containing 400 ng/mL (ng/g) of desmosine. To assess specificity, the 252 non-targeted analytes were extracted from tissue without the addition of desmosine. No interferences were detected. Additionally, desmosine did not contribute to the transition ions for desmosine-$D_4$, nor did desmosine-$D_4$ contribute to the transition ions for desmosine. Unfortified plasma, urine, and tissue matrices following extraction did not contribute or interfere with any monitored MRM transitions.

Dilution Integrity

In cases of low specimen volume or potentially excessive desmosine concentrations that may be encountered in the lung, it was necessary to evaluate the effects of sample dilution. The effects of dilution on the method's bias and precision were evaluated at one concentration (800 ng/mL [ng/g]). This was accomplished by establishing bias and within-run precision studies at dilution ratios of 1:2 in plasma, 1:5 in tissue and 1:10 in urine. All dilutions of fortified matrices met acceptance criteria as denoted in the bias and precision studies.

Sample Stability

Desmosine and desmosine-$D_4$ were evaluated for stability in fortified negative matrix (plasma, urine, and tissue). Five replicates of controls were prepared at a low and high concentration (150 and 800 ng/mL [ng/g]). The extracts were combined and then divided into five different vials. A vial of each level was injected in triplicate on day 0. The other vials were stored on the instrument (in a refrigerated autosampler at 4° C.) and re-injected on days 1, 2, 3 and 4. The response of desmosine, desmosine-$D_4$, and relative responses remained within +20% of the response from day 0. Extract stability was confirmed to be at least 3 days after the date of extraction for desmosine and desmosine-$D_4$.

Upper Limit of Linearity (ULOL) and Carryover

The ULOL (as well as lack of carryover) was determined by the analysis of five extracted replicates. Extracted tissue samples of desmosine were prepared at a high QC concentration of 2500 ng/mL (ng/g). Each mixture was bracketed by solvent vials containing 95:5 water:methanol. The solvents were evaluated for the presence of any compounds injected in the prior mixture; no desmosine was detected. Subsequently, a negative QC sample containing only the internal standard was injected after extracted high control samples to monitor carryover every time a calibration curve was run during the bias and precision studies.

Analysis of Formalin-Fixed and Unfixed Hamster Lungs

The following groups of lungs, both formalin-fixed and unfixed, were analyzed for free desmosine content as part of method validation: 1) Smoke exposure with LPS, 2) Smoke exposure without LPS, 3) Room air exposure with LPS, and 4) Room air exposure without LPS. The results (Table IV and FIG. 5) indicate that the combination of smoke and LPS produced a synergistic increase in free lung desmosine compared to treatment with either smoke or LPS alone. Furthermore, the reduction in lung elastin crosslinks in the Smoke/LPS group is consistent with airspace enlargement as measured by the mean linear intercept (table V) and confirm that free desmosine is a sensitive marker of emphysematous changes.

TABLE IV

Desmosine concentrations in hamster lung

| | Smoke exposure with LPS (n = 6) | Smoke exposure without LPS (n = 2) | Room air exposure with LPS (n = 6,) | Room air exposure without LPS (n = 4) |
|---|---|---|---|---|
| Lung #1 (fixed) | 281.3 | NS | 108.5 | ND |
| Lung #2 (fixed) | 253.1 | NS | 87.9 | NS |
| Lung #3 (fixed) | 446.9 | NS | 133.8 | ND |
| Lung #4 (unfixed) | 209.2 | NS | 42.0 | NS |
| Lung #5 (unfixed) | 620.5 | 88.8 | 130.7 | ND |
| Lung #6 (unfixed) | 343.4 | 101.3 | 55.5 | ND |

Figure 3:
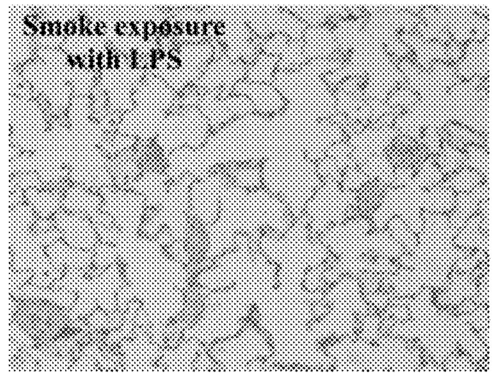
FIG. 3 is a photomicrograph of a smoke-exposed lung after instillation of LPS.
Figure 4:
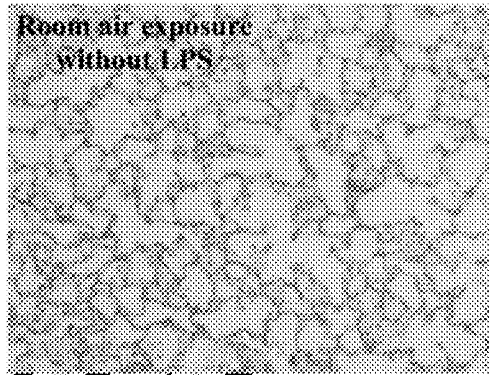
FIG. 4 is a photomicrograph of a control lung exposed only to room air and without instillation of LPS.

LPS, lipopolysaccharide;
LOD, limit of detection;
LOQ, limit of quantification;
NS, no sample available;
ND, not detected FIG. 3 depicts a photomicrograph of a smoke-exposed lung after instillation of LPS, and FIG. 4 shows a photomicrograph of a control lung exposed only to room air and without instillation of LPS for comparison. The smoke/LPS group showed a significant increase in airspace size (as measured by mean linear intercept) compared to the control group.

TABLE V

Mean linear intercept

| Group | Room air only (n = 3) | Smoke + LPS (n = 3) |
|---|---|---|
| Mean Linear Intercept (μm) | 55.7 ± 0.6 | 83.6 ± 0.7* |

*p < 0.0001

Figure 5:
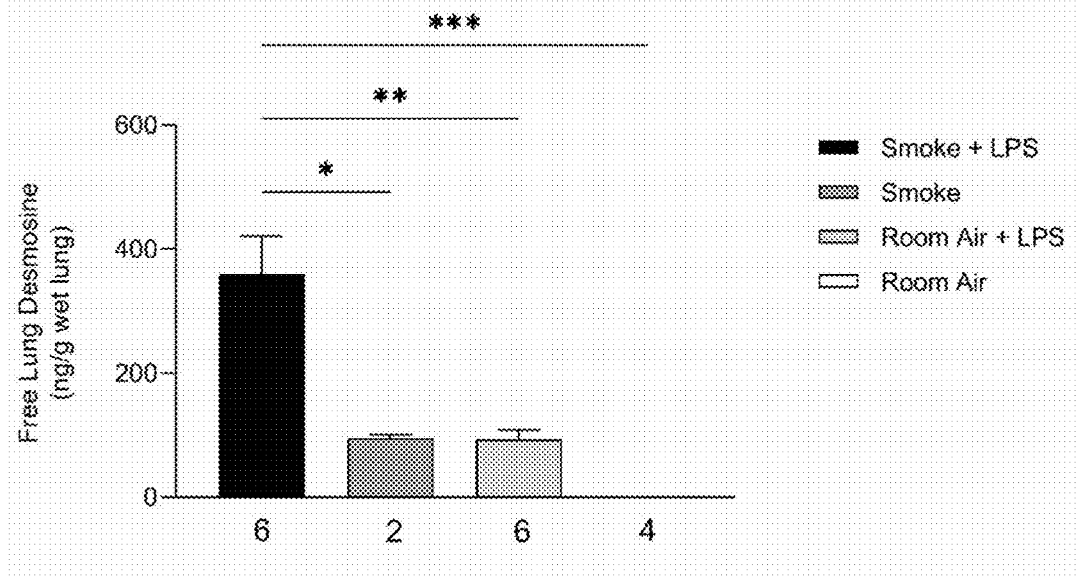
FIG. 5 depicts free desmosine content in the lung.

FIG. 5 provides a graph depicting free desmosine content in the lung. Animals treated with cigarette smoke and intraperitoneal LPS showed a significant increase in desmosine compared with 1) animals exposed to smoke only (*$p<0.05$), 2) animals exposed to room air and given LPS ( $p<0.01$), and 3) animals exposed to room air only (* $p<0.001$). No measurable desmosine was detected in animals exposed to room air only. T-bars indicate standard error of the mean (SEM). Numbers below bars indicate N.

Isodesmosine in the Context of Desmosine Measurements

Prior analytical methods have chromatographically separated desmosine from its structural isomer isodesmosine, however it was previously determined by the authors that such separation might not be justified with respect to its interpretative significance. Desmosine and isodesmosine concentrations are often reported as "desmosine/isodesmosine" as opposed to "desmosine" or "isodesmosine" individually, given that both are elevated in COPD to a very similar extent, and neither desmosine nor isodesmosine is associated with a particular disease apart from one another. Analytically, isodesmosine also shares the exact same MRM transitions as desmosine (526.3→481.2 and 84.1 m/z) and is unable to be spectrally distinguished from desmosine. Baseline separation was not possible for desmosine and isodesmosine under the current method parameters, as their identical chromatographic and mass spectral characteristics cause both crosslinks to co-migrate.

As understood by those of ordinary skill herein, therefore, the present invention therefore can be used to diagnose patients suffering from atherosclerosis, aortic aneurysm, skin lesions, cystic fibrosis, pulmonary hypertension, bronchiectasis, chronic obstructive pulmonary disease (COPD), and COPD exacerbations. Atherosclerosis may be treated, for instance, by a change in diet or exercise, administering a statin or other cholesterol drug, aspirin or medications to lower blood pressure, or invasive procedures such as angioplasty, endarterectomy, fibrinolytic therapy or coronary artery bypass graft surgery.

An aortic aneurysm may be treated surgically, typically by open-chest surgery, aortic root surgery or endovascular aortic aneurysm repair.

Skin lesions may be treated surgically by cryosurgery, excisional surgery, Mohs surgery, or curettage and electrodesiccation or cryotherapy, or nonsurgically by radiation therapy, chemotherapy, photodynamic therapy or biological therapy. Photodynamic therapy is intended to destroy cancer cells with a combination of laser light and drugs that make cancer cells sensitive to light.

Cystic fibrosis may be treated by administering antibiotics, anti-inflammatoires, hypertonic saline, bronchodialators, oral pancreatic enzymes, stool softeners, acid-reducing medications and drugs for diabetes or liver disease. Cystic fibrosis transmembrane conductance regulator (CFTR) modulators may also be administered. CFTR modulators include elexacaftor, ivacaftor, tezacaftor and lumacaftor, taken individually or in combinations of (i) elexacaftor and ivacaftor, (ii) elexacaftor and tezacaftor, (iii) elexacaftor and lumacaftor, (iv) ivacaftor and tezacaftor, (v) ivacaftor and lumacaftor, (vi) elexacaftor, ivacaftor and tezacaftor, (vii) elexacaftor, ivacaftor and lumacaftor, (viii) elexacaftor, tezacaftor and lumacaftor, (ix) ivacaftor, tezacaftor and lumacaftor, and (x) elexacaftor, ivacaftor, tezacaftor and lumacaftor.

Since it is desirable to identify cystic fibrosis patients early, infants and children may also be beneficially evaluated to determine their states of elastic fiber injury. Combination (vi) elexacaftor, ivacaftor and tezacaftor may be beneficial for patients age twelve and over. Combination (iv) ivacaftor and tezacaftor may be beneficial for patients age six and over. Combination (v) ivacaftor and lumacaftor may be beneficial for patients age two years and older. Ivacaftor taken alone may be beneficial for patients age six months and older.

Pulmonary hypertension may be treated surgically by right heart catheterization, atrial septostomy, or lung or heart-lung transplant. Pulmonary hypertension may also be treated nonsurgically by administering vasodilators, guanylate cyclase stimulators, endothelin receptor antagonists, phosphodiesterase 5 inhibitors, calcium channel blockers, blood thinners, digoxin, diuretics and oxygen therapy.

Bronchiectasis may be treated by administering oral or intravenous antibiotics.

Chronic obstructive pulmonary disease (COPD) and COPD exacerbations may be treated by cessation of smoking, by administering medications including both long- and short-acting bronchodilators, inhaled steroids, oral steroids, phosphodiesterase-4 inhibitors, theophylline and antibiotics, and by therapy such as oxygen therapy, pulmonary rehabilitation and use of bilevel positive airway pressure breathing devices. Chronic obstructive pulmonary disease (COPD) and COPD exacerbations may also be treated surgically by lung volume reduction surgery, lung transplant and bullectomy.

REFERENCES

1. Mecham, R. P., (1997) Elastin fibers in the lung. In R. G. Crystal, J. B. West, E. R. Weibel, P. J. Barnes (eds.), Scientific Foundations, Lippincott-Raven, Philadelphia, PA, pp. 729-736.
2. Thomas, J., Elsden, D. F., and Partridge, S. M. (1963) Degradation Products from Elastin: Partial Structure of Two Major Degradation Products from the Cross-Linkages in Elastin. Nature, 200, 651-652.
3. Shimada, W., Bowman, A., Davis, N. R., and Anwar, R. A. (1969) An approach to the study of the structure of desmosine and isodesmosine containing peptides isolated from the elastase digest of elastin. Biochemical and Biophysical Research Communications, 37, 191-197.
4. Akagawa, M. and Suyama, K. (2000) Mechanism of Formation of Elastin Crosslinks. Connective Tissue Research, 41, 131-141.
5. Cocci, F., Miniati, M., Monti, S., Cavarra, E., Gambelli, F., Battolla, L., et al. (2002) Urinary desmosine excretion is inversely correlated with the extent of emphysema in patients with chronic obstructive pulmonary disease. The International Journal of Biochemistry & Cell Biology, 34, 594-604.
6. Luisetti, M., Sturani, C., Sella, D., Madonini, E., Galavotti, V., Bruno, G., et al. (1996) MR889, a neutrophil elastase inhibitor, in patients with chronic obstructive pulmonary disease: a double-blind, randomized, placebo-controlled clinical trial. European Respiratory Journal, 9, 1482-1486.
7. Mcclintock, D. E., Starcher, B., Eisner, M. D., Thompson, B. T., Hayden, D. L, Church, G. D., et al. (1995) Higher urine desmosine levels are associated with mortality in patients with acute lung injury. American Journal of Physiology-Lung Cellular and Molecular Physiology, 291, 566-571.
8. Starcher, B., Green, M., Scott, M. (1995) Measurement of urinary desmosine as an indicator of acute pulmonary disease. Respiration, 62, 252-257.
9. Stone, P. J., Gottlieb, D. J., O'Connor, G. T., Ciccolella, D. E., Breuer, R., Bryan-Rhadfi. J., Shaw, H. A., Franzblau, C., and Snider, G. (1995) Elastin and collagen degradation products in urine of smokers with and without chronic obstructive pulmonary diseases. American Journal of Respiratory and Critical Care Medicine, 151, 952-959.
10. Stone, P. J., Konstan, M. W., Berger, M., Dorkin, H. L., Franzblau, C., and Snider, G. L. (1995) Elastin and collagen degradation products in urine of patients with cystic fibrosis. American Journal of Respiratory and Critical Care Medicine, 152, 157-162.
11. Stone, P. J., Bryanrhadfi, J., Lucey, E. C., Ciccolella, D. E., Crombie, G., Faris, B., et al. (1991) Measurement of urinary desmosine by isotope dilution and high performance liquid chromatography: correlation between elastase-induced air-space enlargement in the hamster and elevation of urinary desmosine. The American Review of Respiratory Diseases, 144, 284-290.
12. Cumiskey, W. R., Pagani, E. D., and Bode, D. C. (1995) Enrichment and analysis of desmosine and isodesmosine in biological fluids. Journal of Chromatography B, 668, 199-207.
13. Ma, S., Turino, G. M., and Lin, Y. Y. (2011) Quantitation of desmosine and isodesmosine in urine, plasma, and sputum by LC-MS/MS as biomarkers for elastin degradation. Journal of Chromatography B, 879, 1893-1898.
14. Albarbarawi, O., Barton, A., Miller, D., McSharry, C., Chaudhuri, R., Thomson, N.C., Palmer, C. N., Devereux, G., and Huang, J. T. (2013) Characterization and validation of an isotope-dilution LC-MS/MS method for quantification of total desmosine and isodesmosine in plasma and serum. Bioanalysis, 5, 1991-2001
15. Ma, S., Turino, G. M., Hayashi, T., Yanuma, H., Usuki, T., and Lin, Y. Y. (2013) Stable deuterium internal standard for the isotope-dilution LC-MS/MS analysis of elastin degradation. Analytical Biochemistry, 440, 158-165.
16. Luisetti, M., Stolk, J., and Iadarola, P. (2012) Desmosine, a biomarker for COPD: old and in the way. European Respiratory Journal, 39, 797-798.
17. Mehraban, S., Gu, G., Ma, S., Liu, X., Turino, G., and Cantor, J. (2020) The Proinflammatory Activity of Structurally Altered Elastic Fibers. American Journal of Respiratory Cell and Molecular Biology, 63, 699-706.
18. Fagiola, M., Avella, J., and Cantor, J. O. (2021) Evaluation of Current LC-MS Based Assays for Desmosine Analysis and Adoption of Non Ion-Paired Reverse-Phase High-Performance Liquid Chromatography. Journal of Chromatographic Sciences.—In review
19. Knudsen, L., Weibel, E. R., Gundersen, H. J. G., et al. (2010) Assessment of air space size characteristics by intercept (chord) measurement: an accurate and efficient sterological approach. Journal of Applied Physiology, 108, 412-421.
20. ASB AAFS Standards Board (2019) ANSI/ASB Standard 036: Standard Practices for Method Validation in Forensic Toxicology (accessed Jan. 14, 2021).
21. Cantor, J., Ochoa, A., Ma, S., Liu, X., Turino, G. (2018) Free Desmosine is a Sensitive Marker of Smoke-Induced Emphysema. Lung, 196, 659-663.
22. Cantor, J., Ma, S., and Turino, G. (2017) A pilot clinical trial to determine the safety and efficacy of aerosolized hyaluronan as a treatment for COPD. International Journal of Chronic Obstructive Pulmonary Disease, 12, 2747-2752.
23. Cantor, J., Ma, S., Liu, X., et al. (2021) A 28-day clinical trial of aerosolized hyaluronan in alpha-1 antiprotease deficiency COPD using desmosine as a surrogate marker for drug efficacy. Respiratory Medicine, 182, 1-7.

What is claimed is:

1. A method of treatment for a disease in a subject suspected of having elastic fiber injury, comprising:

using non-ion-paired liquid chromatography combined with mass spectrometry to measure only the amount of free desmosine and free isodesmosine in a sample from the subject, the sample being at least one member selected from the group consisting of connective tissue matrices, urine, plasma, sputum, bronchoalveolar lavage fluid and exhaled breath condensate; and correlating the measured amount of free desmosine and free isodesmosine to an established range of normal values of free desmosine and free isodesmosine derived from nonsmoking healthy individuals to identify the elastic fiber injury;

determining that the subject suffers from a disease selected from the group consisting of atherosclerosis, aortic aneurysm, skin lesions, cystic fibrosis, pulmonary hypertension, bronchiectasis, chronic obstructive pulmonary disease (COPD), COPD exacerbations and alpha-1 antitrypsin deficiency (AATD); and treating the disease, wherein said treatment for atherosclerosis comprises a change in diet or exercise, administering a statin or other cholesterol drug, aspirin or medications to lower blood pressure, or angioplasty, endarterectomy, fibrinolytic therapy or coronary artery bypass graft surgery, said treatment for aortic aneurysm comprises open-chest surgery, aortic root surgery or endovascular aortic aneurysm repair, said treatment for skin lesions comprises cryosurgery, excisional surgery, Mohs surgery, curettage and electrodesiccation, cryotherapy, radiation therapy, chemotherapy, photodynamic therapy or biological therapy, said treatment for cystic fibrosis comprises administering antibiotics, anti-inflammatories, hypertonic saline, bronchodialators, oral pancreatic enzymes, stool softeners, acid-reducing medications, drugs for diabetes or liver disease, or cystic fibrosis transmembrane conductance regulator modulators, said treatment for pulmonary hypertension comprises right heart catheterization, atrial septostomy, lung or heart-lung transplant, or administering vasodilators, guanylate cyclase stimulators, endothelin receptor antagonists, phosphodiesterase 5 inhibitors, calcium channel blockers, blood thinners, digoxin, diuretics or oxygen therapy, said treatment for bronchiectasis comprises administering oral or intravenous antibiotics, said treatment for COPD and COPD exacerbations comprises cessation of smoking, administering bronchodilators, inhaled steroids, oral steroids, phosphodiesterase-4 inhibitors, theophylline or antibiotics, oxygen therapy, pulmonary rehabilitation, use of bilevel positive airway pressure breathing devices, lung volume reduction surgery, lung transplant or bullectomy.

2. The method according to claim 1, wherein said connective tissue matrices are selected from the group consisting of lung, trachea, bronchi, skin, heart and blood vessels.

3. The method according to claim 1, wherein the COPD is pulmonary emphysema.

4. The method according to claim 3, wherein the subject is a mammal.

5. The method according to claim 4, wherein the subject is a human.

6. The method according to claim 1, wherein the mass spectrometry is liquid chromatography mass spectrometry (LC-MS).

7. The method according to claim 1, wherein the mass spectrometry is liquid chromatography-tandem mass spectrometry (LC-MS-MS).

8. The method of claim 1, wherein said disease is atherosclerosis and said treatment is a change in diet or exercise, administering a statin, aspirin or medication to lower blood pressure, angioplasty, endarterectomy, fibrinolytic therapy or coronary artery bypass graft surgery.

9. The method of claim 1, wherein said disease is aortic aneurysm and said treatment is open-chest surgery, aortic root surgery or endovascular aortic aneurysm repair.

10. The method of claim 1, wherein said disease is a skin lesion and said treatment is cryosurgery, excisional surgery, Mohs surgery, curettage and electrodesiccation, curettage and cryotherapy, radiation therapy, chemotherapy, photodynamic therapy or biological therapy.

11. The method of claim 1, wherein said disease is cystic fibrosis and said treatment is administering antibiotics, anti-inflammatoires, hypertonic saline, bronchodialators, oral pancreatic enzymes, stool softeners, acid-reducing medications, drugs for diabetes or liver disease, or cystic fibrosis transmembrane conductance regulator (CFTR) modulators.

12. The method of claim 11, wherein said CFTR modulators comprise at least one of elexacaftor, ivacaftor, tezacaftor or lumacaftor.

13. The method of claim 12, wherein said CFTR modulators comprise the combinations of (i) elexacaftor and ivacaftor, (ii) elexacaftor and tezacaftor, (iii) elexacaftor and lumacaftor, (iv) ivacaftor and tezacaftor, (v) ivacaftor and lumacaftor, (vi) elexacaftor, ivacaftor and tezacaftor, (vii) elexacaftor, ivacaftor and lumacaftor, (viii) elexacaftor, tezacaftor and lumacaftor, (ix) ivacaftor, tezacaftor and lumacaftor, or (x) elexacaftor, ivacaftor, tezacaftor and lumacaftor.

14. The method of claim 1, wherein said disease is pulmonary hypertension and said treatment comprises right heart catheterization, atrial septostomy, lung-transplant or heart-lung transplant, or administering vasodilators, guanylate cyclase stimulators, endothelin receptor antagonists, phosphodiesterase 5 inhibitors, calcium channel blockers, blood thinners, digoxin, diuretics or oxygen therapy.

15. The method of claim 1, wherein said disease is bronchiectasis and said treatment comprises administering oral or intravenous antibiotics.

16. The method of claim 1, wherein said disease is chronic obstructive pulmonary disease (COPD) or COPD exacerbations and said treatment comprises cessation of smoking, administering long- or short-acting bronchodilators, inhaled steroids, oral steroids, phosphodiesterase-4 inhibitors, theophylline and antibiotics, oxygen therapy, pulmonary rehabilitation, bilevel positive airway pressure breathing devices, lung volume reduction surgery, lung transplant or bullectomy.

17. A method of treatment for an elastic fiber injury, comprising the steps of:

obtaining a specimen of tissue from a subject;

homogenizing said specimen to release free desmosine and free isodesmosine from the tissue;

centrifuging the homogenized specimen to produce a supernatant with sedimented solid material;

adding a desmosine-d4 standard to the supernatant;

separating the free desmosine and free isodesmosine from said supernatant using cation exchange chromatography and obtaining a chromatographic eluent;

applying the chromatographic eluent to a non-ion paired chromatography column;

measuring only free desmosine and free isodesmosine in the chromatographic eluent using tandem mass spectrometry; and comparing measured levels of free desmosine and free isodesmosine in the chromatographic eluent to an established range of normal values of free desmosine and free isodesmosine derived from nonsmoking healthy individuals to identify the elastic fiber injury, wherein said treatment comprises at least one of a change in diet or exercise, administering a statin, aspirin or medication to lower blood pressure, angioplasty, endarterectomy, fibrinolytic therapy, coronary artery bypass graft surgery, open-chest surgery, aortic root surgery, endovascular aortic aneurysm repair, cryosurgery, excisional surgery, Mohs surgery, curettage and electrodesiccation, curettage and cryotherapy, radiation therapy, chemotherapy, photodynamic therapy, biological therapy, administering antibiotics, anti-inflammatoires, hypertonic saline, bronchodialators, oral pancreatic enzymes, stool softeners, acid-reducing medications, drugs for diabetes or liver disease, cystic fibrosis transmembrane conductance regulator (CFTR) modulators, right heart catheterization, atrial septostomy, lung-transplant or heart-lung transplant, administering vasodilators, guanylate cyclase stimulators, endothelin receptor antagonists, phosphodiesterase 5 inhibitors, calcium channel blockers, blood thinners, digoxin, diuretics, oxygen therapy, oral or intravenous antibiotics, cessation of smoking, inhaled steroids, oral steroids, phosphodiesterase-4 inhibitors, theophylline, pulmonary rehabilitation, bilevel positive airway pressure breathing devices, lung volume reduction surgery or bullectomy.

18. A method of treatment for an elastic fiber injury in a tissue from a subject, comprising the steps of:

procuring a suitable specimen of tissue from a subject;

homogenization said tissue to release free desmosine and free isodesmosine therefrom;

centrifuging the homogenized tissue to obtain a supernatant;

adding a desmosine-d4 standard to the supernatant;

separating the free desmosine and free isodesmosine from said supernatant and obtain a chromatographic eluent using cation exchange chromatography;

applying the chromatographic eluent to a non-ion paired chromatography column;

measuring only the free desmosine and free isodesmosine from the non-ion paired chromatography column using tandem mass spectrometry; and comparing measured levels of free desmosine and free isodesmosine in the chromatographic eluent to an established range of normal values of free desmosine and free isodesmosine derived from nonsmoking healthy individuals to identify the elastic fiber injury, wherein said treatment comprises at least one of a change in diet or exercise, administering a statin, aspirin or medication to lower blood pressure, angioplasty, endarterectomy, fibrinolytic therapy, coronary artery bypass graft surgery, open-chest surgery, aortic root surgery, endovascular aortic aneurysm repair, cryosurgery, excisional surgery, Mohs surgery, curettage and electrodesiccation, curettage and cryotherapy, radiation therapy, chemotherapy, photodynamic therapy, biological therapy, administering antibiotics, anti-inflammatorypertonic saline, bronchodialators, oral pancreatic enzymes, stool softeners, acid-reducing medications, drugs for diabetes or liver disease, cystic fibrosis transmembrane conductance regulator (CFTR) modulators, right heart catheterization, atrial septostomy, lung-transplant or heart-lung transplant, administering vasodilators, guanylate cyclase stimulators, endothelin receptor antagonists, phosphodiesterase 5 inhibitors, calcium channel blockers, blood thinners, digoxin, diuretics, oxygen therapy, oral or intravenous antibiotics, cessation of smoking, inhaled steroids, oral steroids, phosphodiesterase-4 inhibitors, theophylline, pulmonary rehabilitation, bilevel positive airway pressure breathing devices, lung volume reduction surgery and bullectomy.

* * * * *